US007642073B2

(12) United States Patent
Rozzell, Jr.

(10) Patent No.: US 7,642,073 B2
(45) Date of Patent: Jan. 5, 2010

(54) METHOD FOR REDUCTIVE AMINATION OF A KETONE USING A MUTATED ENZYME

(75) Inventor: J. David Rozzell, Jr., Burbank, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 11/786,054

(22) Filed: Apr. 9, 2007

(65) Prior Publication Data
US 2008/0076162 A1 Mar. 27, 2008

Related U.S. Application Data

(63) Continuation of application No. 10/039,952, filed on Oct. 24, 2001, now Pat. No. 7,202,070, which is a continuation-in-part of application No. 09/702,421, filed on Oct. 31, 2000, now abandoned.

(60) Provisional application No. 60/288,378, filed on May 3, 2001.

(51) Int. Cl.
*C12P 13/00* (2006.01)

(52) U.S. Cl. ............... 435/128; 435/190; 435/280

(58) Field of Classification Search .................. 435/128, 435/190, 280
See application file for complete search history.

(56) References Cited

U.S. PATENT DOCUMENTS

| 4,518,692 | A | | 5/1985 | Rozzell |
| 4,710,467 | A | | 12/1987 | Wood et al. |
| 4,745,059 | A | | 5/1988 | Voelskow et al. |
| 5,106,740 | A | | 4/1992 | Bader et al. |
| 5,300,437 | A | * | 4/1994 | Stirling et al. ............... 435/280 |
| 5,316,943 | A | | 5/1994 | Kidman et al. |
| 5,605,793 | A | | 2/1997 | Stemmer |
| 5,753,470 | A | | 5/1998 | Then et al. |
| 5,798,234 | A | | 8/1998 | Engel et al. |
| 5,801,006 | A | | 9/1998 | Kaufman |
| 5,811,238 | A | | 9/1998 | Stemmer et al. |
| 5,830,721 | A | | 11/1998 | Stemmer et al. |
| 5,837,458 | A | | 11/1998 | Minshull et al. |
| 5,854,035 | A | | 12/1998 | Stoyan et al. |
| 5,916,786 | A | * | 6/1999 | Rozzell, Jr. ............... 435/155 |
| 5,942,644 | A | * | 8/1999 | Rozzell, Jr. ............... 564/201 |
| 5,958,672 | A | | 9/1999 | Short |
| 5,958,715 | A | | 9/1999 | Muller |
| 5,965,408 | A | | 10/1999 | Short |
| 6,001,574 | A | | 12/1999 | Short et al. |
| 6,030,779 | A | | 2/2000 | Short |
| 6,054,267 | A | | 4/2000 | Short |
| 6,117,679 | A | | 9/2000 | Stemmer |
| 6,207,862 | B1 | * | 3/2001 | Rozzell, Jr. ............... 564/150 |
| 6,255,092 | B1 | | 7/2001 | Kojima et al. |
| 6,365,380 | B2 | | 4/2002 | Liu et al. |
| 6,413,750 | B1 | * | 7/2002 | Hummel et al. ............ 435/190 |
| 6,727,083 | B2 | | 4/2004 | Takashima et al. |
| 7,202,070 | B2 | * | 4/2007 | Rozzell, Jr. ............... 435/191 |
| 2002/0192786 | A1 | | 12/2002 | Yamada et al. |
| 2003/0138930 | A1 | | 7/2003 | Yan et al. |

FOREIGN PATENT DOCUMENTS

WO    WO 00/28007    5/2000

OTHER PUBLICATIONS

Kambourakis, S. et al. Ketoreductases in the Synthesis of Valuable Chiral Intermediates. Tetrahedron vol. 60, No. 3, 663-669, 2004.*
Mansson M. et al. Immobilized Active Coenzymes. Methods in Enzymology 136:3-9, 1987.*
May O. et al. Inverting Enantioselectivity by Directed Evolution of Hydantoinase for Improved Production of L-Methionine. Nature Biotechnology 18:317-320, Mar. 2000.*
Jones, J.B. and Takemura, T. Enzymes in Organic Synthesis. Part 30. Can. J. Chem. 62, 77-80, 1984.
Lemiere, G.L. Alcohol Dehydrogenase Catalysed Oxireduction Reactions in Organic Chemistry, 19-34, D. Reidel Publishing Company, 1986.
May, O. et al. Inverting Enantioselectivity By Directed Evolution of Hydantoinase for Improved Production of L-Methionine. Nat. Biotech. 18, 317-320, 2000. (On Order).
Mansson et al. Immobilized Active Coenzymes. Methods in Enzymology, 136, 3-45, 1987.(On Order).
Nagata, S. et al. Gene Cloning and Sequence Determination of Leucine Dehydrogenase from Bacillus stearothermophilus . . . , Biochemistry, 27, 9056-9062, 1988.
Reddy, G. L., et al. Solid Phase Synthesis of Signal Sequence Fragments . . . Tetrahedron Letters, 26, No. 35, 4257-4260, 1985.
Snaked, Z. and G.M. Whitesides. Enzyme-Catalyzed Organic Synthesis: NADH Regeneration . . . ,J. Am. Chem. Soc., 102, 7104-7105, 1980.
Yamada, H. et al. A novel NADPH-dependent Aldehyde Reductase . . . , FEMS Microbiology Letters, 70, 45-48, 1990.

* cited by examiner

*Primary Examiner*—Ralph Gitomer
(74) *Attorney, Agent, or Firm*—Christie, Parker & Hale, LLP.

(57) ABSTRACT

Methods for chemically transforming compounds using a mutated enzyme are provided, and more particularly a method for the production of an amine from a target ketone. The methods comprise creating a mutated enzyme that catalyzes the reductive amination of the target ketone under conditions sufficient to permit the formation of the desired amine to thereby produce the amine.

3 Claims, No Drawings

METHOD FOR REDUCTIVE AMINATION OF A KETONE USING A MUTATED ENZYME

CROSS-REFERENCE TO RELATED APPLICATION(S)

This application is a continuation of U.S. patent application Ser. No. 10/039,952, filed Oct. 24, 2001 now U.S. Pat. No. 7,202,070, which is a continuation-in-part of U.S. application Ser. No. 09/702,421, filed Oct. 31, 2000 now abandoned, and claims the benefit of U.S. Provisional Application No. 60/288,378, filed May 3, 2001, the entire disclosures of which are incorporated herein by reference.

BACKGROUND OF THE INVENTION

Enzymes are proteins that are capable of catalyzing chemical transformations. Enzymes position a substrate or substrates in an optimal configuration and stabilize the transition state in the reaction pathway, thereby determining which of several potential chemical transformations actually occurs. Enzymes can be highly specific, both in terms of the reaction that occurs and in their choice of substrate. Enzymes often accelerate reactions by factors of more than a million. Because of their specificity and catalytic power, enzymes are increasingly being used for industrial applications.

One family of enzymes that is especially useful for industrial applications is the family of oxidoreductase enzymes. Oxidoreductases catalyze redox reactions, such as the reduction of aldehydes and ketones to alcohols, the reductive amination of ketones, aldehydes, and ketoacids to amines and amino acids, the reduction of disulfides to thiols, the reduction of alkenes to alkanes and the like. These reactions are normally reversible, and frequently the same enzymes catalyze the corresponding oxidation reactions. For example, alcohol dehydrogenases and carbonyl reductases catalyze both the reduction of aldehydes and ketones to alcohols and the oxidation of alcohols to aldehydes and ketones. Amino acid dehydrogenases catalyze the oxidation of amino acids to 2-ketoacids and the reductive amination of 2-ketoacids in the presence of ammonium salts to amino acids. Similarly, disulfide reductases catalyze the oxidation of thiols to disulfides or mixed disulfides. Reduction and oxidation reactions are collectively referred to herein as "redox reactions."

Some oxidoreductases can be used to produce fine and specialty chemicals, and are especially useful for producing chiral intermediates in the pharmaceutical and agricultural industries. Oxidoreductases, like many other enzymes, require other molecules, such as cofactors and cosubstrates, for optimal activity. For example, mixed function oxidases use nicotinamide cofactors as part of the complex catalysis of a hydroxylation reaction for the production of chiral alcohols.

Although a number of different enzymes are known, the development of new applications for enzymes such as oxidoreductases requires an expanded search for new enzymes that catalyze specific reactions of interest. For example, amino acid dehydrogenases that reductively aminate certain 2-ketoacids to naturally occurring L-amino acids are known, but no suitable amino acid dehydrogenase has been identified for the production of many non-naturally occurring amino acids. The enzyme catalyzed reductive amination of ketones that are not 2-ketoacids is comparatively quite rare. Similarly, the stereoselective reduction of ketones catalyzed by alcohol dehydrogenases, ketoreductases and carbonyl reductases is known for certain ketones, but enzymes are not available for catalyzing this reaction with many desired target ketones. Transaminases are known that catalyze the transamination of many 2-ketoacids to alpha-amino acids, but certain target 2-ketoacids, particularly those corresponding to non-naturally occurring amino acids, are transaminated poorly, if at all.

There are several known methods to generate potential enzymes that catalyze specific reactions of interest. For example, diverse populations of enzymes can be found in microorganisms harvested from different environments. These microorganisms can be cultured, and their DNA extracted, amplified by PCR, and cloned into a host for expression of the enzymes. Alternatively, various molecular biology techniques, such as mutagenesis, shuffling, molecular breeding, and gene reassembly, can be used to create vast numbers of mutant versions of an enzyme encoded by a known gene. Examples of gene shuffling and molecular breeding are described in U.S. Pat. No. 5,605,793; U.S. Pat. No. 5,811,238; U.S. Pat. No. 5,830,721; U.S. Pat. No. 5,837,458; U.S. Pat. No. 5,965,408; U.S. Pat. No. 5,958,672; U.S. Pat. No. 6,001,574; and U.S. Pat. No. 6,117,679, all incorporated herein by reference. Examples of methods for constructing large numbers of mutants are described in U.S. Pat. No. 6,001,574; U.S. Pat. No. 6,030,779; and U.S. Pat. No. 6,054,267, also incorporated herein by reference.

Once potential enzymes that may be able to catalyze specific reactions of interest have been generated, the enzymes are tested for activity on the desired substrate, or target compound. Because many enzymes such as oxidoreductases require nicotinamide cofactors for optimal activity, detection of the oxidation or reduction of the cofactor can be used as a signal of enzyme activity.

Currently, the most common method of detecting enzymes using nicotinamide cofactors involves the direct measurement of the cofactor. For example, as a carbonyl reductase reduces a carbonyl group, the concomitant oxidation of reduced nicotinamide, i.e., the conversion of a reduced form of nicotinamide adenine dinucleotide (NADH) to nicotinamide adenine dinucleotide (NAD+) or the conversion of a reduced form of nicotinamide adenine dinucleotide phosphate (NADPH) to nicotinamide adenine dinucleotide phosphate (NADP+) can be detected using the absorbance of the reduced form of the cofactor. This reaction of the cofactor can be monitored in a solution by observing the decrease in the absorbance of the solution at 340 nm using a spectrophotometer. Alternatively, during the carbonyl reductase-catalyzed oxidation of an alcohol to the corresponding aldehyde or ketone, NAD+ is converted to NADH or NADP+ is converted to NADPH. The reduction of the cofactor can be detected by monitoring the increase in absorbance at 340 nm, corresponding to the increase in concentration of reduced nicotinamide cofactor. Similarly, fluorescence measurements of nicotinamide cofactors can be performed as well. Additionally, the change in concentration of oxidized or reduced nicotinamide cofactor can be used to detect other enzymes catalyzing cofactor-requiring reactions of interest.

Detection of enzymatic activity is often performed on many enzyme sources for a particular reaction of interest in a process called screening. Often when screening, and particularly when carrying out high throughput screening, mixtures of cells or cell lysates containing suspended insoluble material are used as potential sources for new enzymes because clarification of the crude mixtures is operationally difficult. The difficulty in using such crude mixtures for routine screening for nicotinamide cofactor-using enzymes is that the reaction mixtures contain suspended solid material in the form of cells or cell debris. This insoluble material impedes the transmission of light through the solution and causes high background readings in the absorbance measurements of the cofactors. The crude mixtures also contain various cellular metabolites and biochemicals that absorb at 340 nm, further compromising the accuracy of the measurements. These issues are even more problematic when using high throughput screening methods due to the small volumes used in high density array formats such as microtiter plates or chips. Similarly, if fluorescence measurements are carried out, detecting the emission of fluorescence is also impeded by the presence of insoluble material.

As an alternative, the products of the desired enzymatic reaction can be detected directly by chromatographic techniques. This method requires sampling each individual reaction followed by chromatographic separation of the reaction products, which may include alcohols, carbonyl compounds, and the like. Such a procedure is complex and time-consuming and is impractical for high throughput screening assays when many enzyme sources are tested for the desired enzymatic activity.

SUMMARY OF THE INVENTION

The present invention provides novel methods for chemically transforming compounds using a mutated enzyme. In one embodiment, the invention is directed to a method for the production of an amino acid from a target 2-ketoacid. The method comprises creating a mutated enzyme that catalyzes the reductive amination or transamination of the target 2-ketoacid; and providing the mutated enzyme in a reaction mixture comprising the target 2-ketoacid under conditions sufficient to permit the formation of the amino acid to thereby produce the amino acid.

In another embodiment, the invention is directed to a method for the production of an amine from a target ketone. The method comprises creating a mutated enzyme that catalyzes the reductive amination or transamination of the target ketone; and providing the mutated enzyme in a reaction mixture comprising the target ketone under conditions sufficient to permit the formation of the amine to thereby produce the amine.

In yet another embodiment, the invention is directed to a method for the production of an alcohol from a target ketone. The method comprises creating a mutated enzyme that catalyzes the reduction of the target ketone; and providing the mutated enzyme in a reaction mixture comprising the target ketone under conditions sufficient to permit the formation of the alcohol to thereby produce the alcohol.

In the above embodiments, the mutated enzyme may be created by providing an existing enzyme and mutating the existing enzyme to produce the mutated enzyme. The activity of the mutated enzyme on the target 2-ketoacid or ketone is determined by contacting the mutated enzyme with a composition comprising the target 2-ketoacid or ketone and thereafter determining whether there is a change in the pH of the composition. Thereafter, it is determined whether the mutated enzyme has more activity than the existing enzyme on the target 2-ketoacid or ketone. The existing enzyme and/or mutated enzyme can be present in a composition containing whole cells, cell extracts, cell lysates, mixtures containing insoluble cells, particulates, cellular debris, or the like. Other compounds in the composition that also absorb light at 340 nm do not interfere with the detection of enzymatic activity using the method of the present invention because the pH change can be determined, for example, by observing a color change at a different wavelength. Further, the wavelength of the color change can be selected by using an appropriate pH indicator.

DETAILED DESCRIPTION

The present invention is directed to methods for chemically transforming compounds using a mutated enzyme. In particularly preferred embodiments, the invention is directed to a method for the production of an amino acid from a target 2-ketoacid, the production of an amine from a target ketone and the production of an alcohol from a target ketone. The inventive method comprises creating a mutated enzyme that catalyzes the reductive amination or transamination of the target 2-ketoacid or ketone or the reduction of the target ketone and providing the mutated enzyme in a reaction mixture comprising the target 2-ketoacid or ketone under conditions sufficient to permit the formation of the desired amino acid, amine or alcohol to thereby produce the amino acid, amine or alcohol.

As used herein, the terms "mutated" and "mutating" refer broadly to any of a variety of molecular biology techniques, such as mutagenesis, shuffling, molecular breeding, and gene reassembly, that can be used to create vast numbers of mutant versions of an enzyme encoded by a known gene. The activity of the mutated enzyme on the target compound is determined by contacting the mutated enzyme with a composition comprising the target compound and thereafter determining whether there is a change in the pH of the composition. Thereafter it is determined whether the mutated enzyme has more activity than the existing enzyme on the target compound.

By determining in which reactions the pH indicator undergoes a color change, enzymes with the desired enzymatic activity can be detected easily, even in a high throughput format, enabling the more facile discovery of new enzymes, particularly oxidoreductases that catalyze useful redox reactions.

Non-limiting examples of sources of material that can be screened to obtain the existing enzyme include microorganisms, such as bacteria and yeast, which naturally express oxidoreductases, and genetically modified microorganisms, which express wild-type, modified or mutated oxidoreductases. Examples of useful materials to be screened include cell lysates, mixtures of cells, cell extracts, environmental samples and isolates, and the like. The material may be provided as a solution, a suspension, a dried mixture, a solid, or the like. As a solution or suspension, the composition to be screened may be prepared and stored as a solution or as a suspension in liquid form. The composition may be maintained at room temperature, at refrigerator temperatures, or frozen. As a solid or dried mixture, the composition may be prepared by lyophilization or evaporation of a liquid composition. Alternatively, the solid composition may be prepared by mixing solid ingredients such as a cofactor, a pH indicator, and a target compound. When a solid composition is used in the practice of the present invention, the solid composition is normally redissolved or resuspended prior to use by the addition of water or water containing buffer.

As used herein, "target compound" refers to a substance that is desired to be acted upon by an enzyme as a substrate. Typical target compounds include aldehydes, ketones, disulfides, thiols, ketoacids, amines, amino acids, alcohols, alkenes, alkanes, and the like. In connection with the inventive methods, the term "target compound" does not include enzyme substrates that undergo a hydrolytic transformation that results in the creation or removal of an acidic or basic functionality, such as a carboxylic acid group. Target compounds are often chiral and/or transformed into chiral compounds by enzymes, and enrichment in single stereoisomers can occur.

As used herein, the term "pH indicator" means any material or substance that changes its properties in response to a change in pH. Preferred changes in properties include a change in optical properties, such as a color change. Examples of pH indicators useful in the practice of the present invention include, but are not limited to, cresol red, m-cresol purple, bromothymol blue, bromophenol red, bromophenol blue, phenol red, and phenolphthalein. The pH indicator can be selected independently for each screen to determine the pH range or match a desired pH range for the enzyme to be detected. For example, m-cresol purple is yellow at a pH of about 7.4 and purple at a pH of about 9.0. Cresol red is yellow at a pH of about 7.2 and red at a pH of about 8.8. Bromothymol blue is yellow at a pH of about 6.0 and red at a pH of about 7.6. Bromophenol red is yellow at a pH of about 5.2 and red at a pH of about 6.8. Bromophenol blue is yellow at a pH of about 3.0 and blue at a pH of about 4.6. Phenol red is yellow at a pH of about 6.8 and red at a pH of about 8.2. Phenolphthalein is colorless at a pH of about 8.0 and pink at a pH of about 9.8. Other pH indicators can be selected depending on the desired pH range for the reaction and the desired color change.

The conditions of the determination step can be adjusted to favor the detection or screening of an enzyme with a desired pH optimum by adjusting the pH of the reaction mixture used in the screen. For example, when an amino acid dehydrogenase that functions at pH 6 is sought, the reagent composition used for the screen can be buffered at a pH of 6 using a buffer that has its optimum buffering capacity near pH 6, and a pH indicator can be selected that changes color within the range of pH 5 to 7. Similarly, when an alcohol dehydrogenase that catalyzes the oxidation of a target alcohol at pH 9 is sought, the reagent composition used for the screen can be buffered at a pH of 9 using a buffer that has its optimum buffering capacity near pH 9, and a pH indicator can be selected that changes color within the range of pH 8 to 10. Typically, the pH indicator is selected such that it exhibits a color change in response to a change in pH within a range of about 1 to 1.5 pH units on either side of the desired pH for the reaction.

If a buffer is used, the concentration of the buffer is preferably adjusted in order to maintain a desired initial pH for the screening reaction mixture and to reduce or eliminate small changes in pH not caused by the desired redox reaction. However, the concentration of the buffer should not be so high as to impede the change of pH that occurs as the reaction catalyzed by the oxidoreductase proceeds. The buffer may be any substance that helps maintain the desired initial pH of the solution. Examples include potassium phosphate, sodium phosphate, potassium borate, sodium borate, sodium acetate, potassium acetate, sodium bicarbonate, potassium bicarbonate, sodium carbonate, potassium carbonate, TRIS, PIPES, HEPES, MOPS, TEA, CHES, and the like. A listing of some useful biological buffers along with the pH ranges at which they are most effective as buffers can be found in the Catalog of Biochemicals and Reagents for Life Science Research; Sigma Chemical: St, Louis, 1998; p 1871. Often, desirable buffer concentrations must be determined experimentally. However, typical buffer concentrations using the method of the present invention are from about 0.01 mM to about 20 mM, and preferably from about 0.05 mM to about 5 mM.

The above-described method can be used to determine activity of any enzyme that causes a pH change when it catalyzes the reaction of a target compound, and preferably is used to determine activity of oxidoreductases. As used herein, "oxidoreductase" refers to an enzyme capable of performing an oxidation reaction or reduction reaction. Nonlimiting examples of oxidoreductases include a reductase, an oxidase, a dehydrogenase, a ketoreductase, an alcohol dehydrogenase, a carbonyl reductase, an aldehyde dehydrogenase, an amino acid dehydrogenase, an amine oxidase, a disulfide reductase, an enoate reductase, and a mixed function oxidase. A listing of such enzymes can be found in Enzyme Nomenclature; Webb, E. C., Ed. Academic: Orlando 1984; pp 20-141, the disclosure of which is incorporated herein by reference.

Often enzymes, and particularly oxidoreductases, require cofactors or cosubstrates for optimal activity. As used herein, the term "cofactor" means any molecule that participates in a chemical transformation of the target compound, including cofactors and cosubstrates. Nonlimiting examples of cofactors include nicotinamide cofactors, flavins, and derivatives and analogs thereof.

As used herein, "nicotinamide cofactor" refers to any type of the oxidized and reduced forms of nicotinamide adenine dinucleotide (NAD+ and NADH, respectively) and the oxidized and reduced forms of nicotinamide adenine dinucleotide phosphate (NADP+ and NADPH, respectively) and derivatives and analogs thereof. With regard to a nicotinamide cofactor, the term "derivative" means any compound containing a pyridine structural element, including nicotinamides that have been chemically modified by attachment to soluble or insoluble polymeric materials. Some examples of derivatives of nicotinamide cofactors are described in U.S. Pat. No. 5,106,740, and Mansson and Mosbach Methods in Enzymology (1987) 136, 3-45, the disclosures of which are incorporated herein by reference. The term "analogs," as used herein, refers to materials that undergo a formal hydride transfer in a redox reaction similar to that undergone by nicotinamide cofactors. Examples of analogs of nicotinamide cofactors useful in the practice of the present invention include compounds described in U.S. Pat. No. 5,801,006, the disclosure of which is incorporated herein by reference. Other suitable cofactors, as defined herein, can be used in the practice of the invention, as would be recognized by those skilled in the art.

In the practice of the invention, the nicotinamide cofactors can be used in equimolar quantities relative to the target ketone, alcohol, amine or amino acid, or the cofactors may be recycled, if desired. Numerous methods for the recycling of nicotinamide cofactors are well-known in the art, and any of these methods may be used in the practice of the present invention. Some of the methods for recycling nicotinamide cofactors are described in G. L. Lemiere, et al., Tetrahedron Letters, 26, 4257 (1985); in "Enzymes as Catalysts for Organic Synthesis," pp. 19-34, M. Schneider, Ed., Reidel Dordecht, 1986; in Z. Shaked and G. M. Whitesides, J. Am. Chem. Soc. 102, 7104-5 (1980); and J. B. Jones and T. Takamura, Can. J. Chem. 62, 77 (1984); the disclosures of which are incorporated herein by reference. In the use of these recycling methods, an amount of about 0.0001 mole to about 0.05 mole of nicotinamide cofactor is used per mole of ketone to be reduced or reductively aminated, per mole of 2-ketoacid to be reductively aminated, or per mole of alcohol or amine or amino acid to be oxidized, providing a recycle number for the cofactor of from about 20 to about 10,000.

As an example of an oxidoreductase-catalyzed transformation, the reaction for the reduction of a ketone to a chiral alcohol is shown in Scheme 1.

Scheme 1

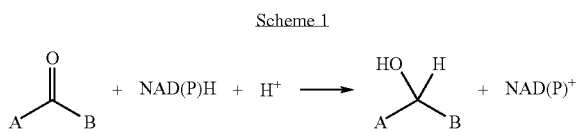

In the above scheme, and the schemes set forth below, A and B are independently selected from hydrogen, alkyl, substituted alkyl, aryl, substituted aryl, heterocyclic, and the like. As shown in the balanced equation in Scheme 1, one proton is consumed in the reaction for each molecule of nicotinamide cofactor oxidized and each molecule of alcohol formed. As the reaction progresses, the consumption of protons causes the pH of the reaction mixture to rise. By including a suitable pH indicator in the reaction mixture, the presence of an alcohol dehydrogenase is indicated by a change in color of the reaction mixture. Although positive reactions can be detected spectrophotometrically, if desired, the use of a colorimetric pH indicator has the added advantage that the presence of oxidoreductase enzymes can be detected visually and without expensive instrumentation.

Because of the reversibility of most reactions catalyzed by oxidoreductases, an oxidation reaction can also be used for screening and detection. For example, an alcohol dehydrogenase or carbonyl reductase catalyzes the oxidation of an alcohol to form an oxidized carbonyl compound, shown in Scheme 2.

Scheme 2

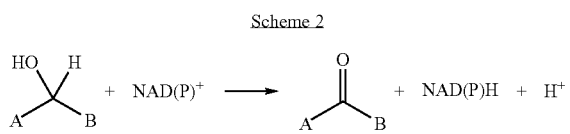

Thus, the presence of an oxidoreductase catalyzing this reaction can be detected using a reaction mixture containing an oxidized nicotinamide cofactor, an alcohol, and a pH indicator. In this case, the pH of the reaction mixture will decrease as the reaction progresses, and the decrease in pH is detected by the change in color of the pH indicator.

As used herein, the term "carbonyl compound" means any chemical compound that has incorporated into it a functional group consisting of a carbon-oxygen double bond. The terms "carbonyl reductase", "ketoreductase", and "alcohol dehydrogenase" mean any enzyme that can catalyze the chemical reduction of a carbonyl group in the presence of a nicotinamide cofactor.

With oxidoreductases that produce amines and amino acids by reductive amination, ammonia or ammonium ion is also a reactant. Thus, when screening for an amine or amino acid dehydrogenase using the method of the present invention, ammonia or a salt of ammonium ion is also included with a pH indicator, a reduced nicotinamide cofactor, and a ketone or ketoacid to be reductively aminated. The reaction is shown in Scheme 3.

Scheme 3

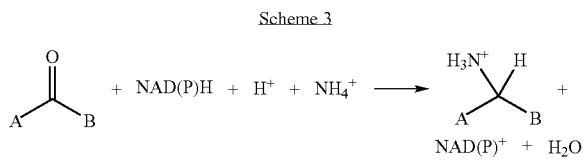

For detection of an amine or amino acid dehydrogenase that can oxidize an amine or amino acid to the corresponding ketone or ketoacid using then method of the present invention, the reaction mixture for detection contains a pH indicator, an oxidized nicotinamide cofactor, and an amine or amino acid to be oxidized. The reaction for the oxidation of an amine or amino acid using an amine or amino acid dehydrogenase is depicted in Scheme 4

Scheme 4

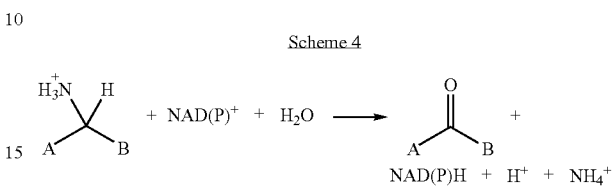

The above-described method can be used to detect enzymes using a second reaction that can be coupled to the enzyme-catalyzed reaction to be screened. For example, in screening for an aminotransferase that catalyzes the transamination of a ketone or ketoacid with L-aspartic acid as the donor, the reaction products are an amine or amino acid and oxaloacetate. In a second reaction, the oxaloacetate can be decarboxylated to pyruvate, with the consumption of a proton. Thus, aminotransferase activity can be detected by detecting an increase in the pH of the reaction mixture because the decarboxylation of oxaloacetate is coupled to the transamination reaction to be screened.

This method is particularly useful for screening for enzymes to perform specific chemical transformations of target compounds that are intermediates in chemical syntheses. Thus, after an enzyme has been determined to have activity for a particular target compound, it can be used to convert that target compound to a useful chemical intermediate, as described above. Useful chemical intermediates include alcohols, amines, alpha-amino acids, beta-amino acids, gamma-amino acids, aldehydes, ketones, carboxylic acids, esters, amides, and the like.

As discussed above, enzymes often require cofactors or cosubstrates for optimal activity. Accordingly, when converting a target compound, preferably a cofactor is present with the enzyme. Suitable cofactors are set forth above.

In the pharmaceutical industry, it is often desirable to chemically transform target compounds into one stereoisomer to the substantial exclusion of another. More specifically, it is desirable to obtain these compounds in more than about 90% enantiomeric excess (ee), preferably in about 95% ee, and still more preferably in about 98% ee, because of the considerable difficulty and the tremendous waste of material in separating enantiomeric products from a racemic mixture. Because enzymes can perform chemical transformations exclusively forming one enantiomeric product and often are easier to use and more cost-effective than performing an asymmetric synthesis, new enzymes that can act upon target compounds are sought after, such as a carbonyl reductase that produces of a single stereoisomer of a alcohol in 98% ee.

In a particularly preferred embodiment, the target compound is a ketone that is not a ketoacid, and the target compound is converted to an amine, preferably a chiral amine, in the presence of an amine dehydrogenase. Preferably the above-described screening method is used to first determine enzymatically-active amino acid dehydrogenases. Further screening is then performed on the enzymatically-active amino acid dehydrogenases, again, in accordance with the procedures described above, to identify enzymatically-active amine dehydrogenases. The thus identified enzymatically-active amine dehydrogenase is then provided in a solution together with a ketone, ammonia and reduced nicotinamide cofactor to synthesize an amine.

The invention is now further described by the following examples, which are given here for illustrative purposes only and are not intended to limit the scope of the invention.

EXAMPLES

Example 1

General procedure for detection of an enzyme that reduces the target compound ethyl-4-chloro-3-ketobutyrate A gene encoding the alcohol dehydrogenase YPR1 (described by Nakamura, K., et al., Bioscience, Biotechnology and Biochemistry, (1997) 61, 375-377), is subjected to mutagenesis by error-prone PCR according to the method of May, O., et al., (Nature Biotechnology, (2000) 18, 317-320). The error-prone PCR is performed in a 100 μL reaction mixture containing 0.25 ng of plasmid DNA as a template dissolved in PCR buffer (10 mM TRIS, 1.5 mM MgCl2, 50 mM KCl, pH 8.3), and also containing 0.2 mM of each dNTP, 50 pmol of each primer and 2.5 units of Taq polymerase (Roche Diagnostics, Indianapolis, Ind.). Conditions for carrying out the PCR are as follows: 2 minutes at 94 °C; 30 cycles of 30 sec 94 °C, 30 sec 55 °C; 2 minutes at 72 °C. The PCR product is double digested with Nco I and Bgl II and subcloned into pBAD/HisA vector (Invitrogen, Carlsbad, Calif.) which has been digested with the same restriction enzymes. The resulting YPR1 mutant library is transformed into the *E. coli* host strain LMG194 (Invitrogen, Carlsbad, Calif.) and plated on LB agar supplied with 100 µg/mL ampicillin. Individual transformants are inoculated into 96-well microtiter plates (hereafter referred to as master plates) containing 0.2 mL LB Broth with 100 µg/mL ampicillin, and growth is allowed to take place for 8 to 16 hours at 37 °C with shaking at 200 rpm. Each well in each master plate is then re-inoculated by a replica plating technique into a new second stage 96-well plate pre-loaded with the same growth media plus 2 g/L of arabinose, and growth is allowed to continue for 5-10 hours at 37 °C with shaking at 200 rpm. The second stage plates are then centrifuged at 14,000 rpm for 20 minutes, and the supernatant is decanted. The cell pellet in each well is washed with 200 μL of water. The washed cell pellet is suspended in 30 μL of B-Per Bacterial Protein Extraction Reagent (Pierce Chemical Co., Rockford, Ill.), hereinafter "B-Per." After mixing, the suspension of cells in B-Per reagent is allowed to stand for 10 minutes at room temperature, and a reaction solution having the following composition is then added to each well in the plate:
7.5 µL of a pH 6.5 solution containing 8 µg/mL of NADPH
7.5 µL of a pH 6.5 50% DMSO solution containing 0.25 M ethyl-4-chloro-3-ketobutyrate
155 µL of 1 mM potassium phosphate buffer, pH 6.5
1.5 µL of a 4 µg/mL solution of cresol red indicator
Wells containing an alcohol dehydrogenase that catalyzes the reduction of the target compound ethyl-4-chloro-3-ketobutyrate can be identified easily as their color changes from an initial yellow to an orange or red color. These wells are correlated to the original wells in the master plates to obtain the original clones of mutant alcohol dehydrogenase that catalyzes the desired reduction reaction.

Example 2

Detection of an enzyme that reduces the target compound ethyl-3-phenyl-3-ketopropionate The procedure of Example 1 is repeated, replacing the ethyl-4-chloro-3-ketobutyrate with ethyl-3-phenyl-3-ketopropionate, thereby identifying at least one mutant alcohol dehydrogenase that catalyzes the desired reduction reaction.

Example 3

Detection of an enzyme that reduces the target compound ethyl-indan-2-one-1-carboxylate The procedure of Example 1 is repeated, replacing the ethyl-4-chloro-3-ketobutyrate with ethyl-indan-2-one-1-carboxylate, thereby identifying at least one mutant alcohol dehydrogenase that catalyzes the desired reduction reaction.

Example 4

Detection of an enzyme that reduces the target compound ethyl-4-phenyl-4-ketobutyrate The procedure of Example 1 is repeated, replacing the ethyl-4-chloro-3-ketobutyrate with ethyl-4-phenyl-4-ketobutyrate, thereby identifying at least one mutant alcohol dehydrogenase that catalyzes the desired reduction reaction.

Example 5

Detection of an enzyme that reduces the target compound ethyl-3-phenyl-3-ketopropionate The procedure of Example 1 is repeated, replacing the reaction solution with a reaction solution of the following composition:
7.5 µL of a pH 6.5 solution containing 8 µg/mL of NADPH
7.5 µL of pH 6.5 DMSO solution containing 0.25 M ethyl-3-phenyl-3-ketopropionate
155 µL of a 1 mM potassium phosphate buffer, pH 7.0
1.5 µL of a 4 µg/mL solution of a cresol red indicator
Wells containing an alcohol dehydrogenase that reduces ethyl-3-phenyl-3-ketopropionate can be identified easily as the color changes from an initial yellow to a red color. At least one mutant alcohol dehydrogenase that catalyzes the desired reduction reaction is identified.

Example 6

Detection of an enzyme that reduces the target compound ethyl-indan-2-one-1-carboxylate The procedure of Example 5 is repeated, replacing the ethyl-3-phenyl-3-ketopropionate with ethyl-indan-2-one-1-carboxylate, thereby identifying at least one mutant alcohol dehydrogenase that catalyzes the desired reduction reaction.

Example 7

Detection of an enzyme that reduces the target compound ethyl-4-phenyl-4-ketobutyrate The procedure of Example 5 is repeated, replacing the ethyl-3-phenyl-3-ketopropionate with ethyl-4-phenyl-4-ketobutyrate, thereby identifying at least one mutant alcohol dehydrogenase that catalyzes the desired reduction reaction.

Example 8

Detection of an enzyme that reduces the target compound ethyl-cyclohexanone-2-carboxylate The procedure of Example 5 is repeated, replacing the ethyl-3-phenyl-3-ketoproponiate with ethyl-cyclohexanone-2-carboxylate, thereby identifying at least one mutant alcohol dehydrogenase that catalyzes the desired reduction reaction.

Example 9

Detection of an enzyme that reduces the target compound ethyl-2-ethyl-3-ketobutyrate The procedure of Example 1 is repeated, replacing the reaction solution with a reaction solution of the following composition:
7.5 μL of a pH 6.5 solution containing 8 μg/mL of NADPH
7.5 μL of a pH 6.5 50% DMSO solution containing 0.25 M ethyl-2-ethyl-3-ketobutyrate
155 μL of a 2 mM potassium phosphate buffer, pH 6.5
1.5 μL of a 4 μg/mL solution of bromothymol blue indicator
Wells containing an alcohol dehydrogenase that reduces ethyl-2-ethyl-3-ketobutyrate can be identified easily as the color changes from an initial yellow to a blue color.

Example 10

Detection of an enzyme that reduces the target compound ethyl-2-allyl-3-ketobutyrate The procedure of Example 9 is repeated, replacing the ethyl-2-ethyl-3-ketobutyrate with ethyl-2-allyl-3-ketobutyrate, thereby identifying at least one mutant alcohol dehydrogenase that catalyzes the desired reduction reaction.

Example 11

Detection of an enzyme that reduces the target compound ethyl-2-phenyl-3-ketobutyrate The procedure of Example 9 is repeated, replacing the ethyl-2-ethyl-3-ketobutyrate with ethyl-2-phenyl-3-ketobutyrate, thereby identifying at least one mutant alcohol dehydrogenase that catalyzes the desired reduction reaction.

Example 12

Detection of an enzyme that reduces the target compound ethyl-2-benzyl-3-ketobutyrate The procedure of Example 9 is repeated, replacing the ethyl-2-ethyl-3-ketobutyrate with ethyl-2-benzyl-3-ketobutyrate, thereby identifying at least one mutant alcohol dehydrogenase that catalyzes the desired reduction reaction.

Example 13

Detection of an Enzyme that Oxidizes a Target Compound Alcohol

A gene encoding the alcohol dehydrogenase Alr1 (Yamada, et al., FEMS Microbiology Letters, (1990) 70, 45-48) is subjected to mutagenesis by error-prone PCR according to the method of May et al. The error-prone PCR is performed in a 100 μL reaction mixture containing 0.25 ng of plasmid DNA as template dissolved in PCR buffer containing 0.2 mM of each dNTP, 50 pmol of each primer and 2.5 units of Taq polymerase. Conditions for carrying out the PCR are as follows: 2 minutes at 94 °C; 30 cycles of 30 sec 94 °C, 30 sec 55 °C; 2 minutes at 72 °C. The PCR product is double digested with Nco I and Bgl II and subcloned into pBAD/HisA vector which has been digested with the same restriction enzymes. The resulting Alr1 mutant library is transformed into an *E. coli* host strain LMG194 and plated on LB agar supplied with 100 μg/mL ampicillin. Individual transformants are inoculated into master plates containing 0.2 mL LB Broth with 100 μg/mL ampicillin, and growth is allowed to take place for 8-16 hours at 37 °C with shaking at 200 rpm. Each well in each master plate is then re-inoculated by a replica plating technique into a new second stage 96-well plate pre-loaded with the same growth media plus 2 g/L of arabinose, and growth is allowed to continue for 5 to 10 hours at 37 °C with shaking at 200 rpm. The second stage plates are then centrifuged at 14,000 rpm for 20 minutes, and the supernatant is decanted. The cell pellet in each well is washed with 200 μL of water. The washed cell pellet is suspended in 30 μL of B-Per. After mixing, the suspension of cells in B-Per reagent is allowed to stand for 10 minutes at room temperature, and a solution having the following composition is then added to each well in the plate:
7.5 μL of a pH 8.0 solution containing 20 μg/ml of NADP+
7.5 μL of a pH 8.0 50% DMSO solution containing 0.25 M (2R,3S)-ethyl-2-ethyl-3-hydroxybutyrate
155 μL of 2 mM potassium phosphate buffer, pH 8.0
1.5 μL of a 4 μg/ml solution of bromothymol blue indicator Wells in which the color changes from an initial blue to a yellow color contain mutant alcohol dehydrogenases that catalyze the oxidation of the target alcohol (2R,3S)-ethyl-2-ethyl-3-hydroxybutyrate. These wells are correlated to the original wells in the master plates to obtain the original clones of mutant alcohol dehydrogenases catalyzing the desired oxidation reaction.

Example 14

General procedure for detection of an enzyme that reductively aminates the target compound 3,3-dimethyl-2-ketobutyrate A gene encoding leucine dehydrogenase from *B. stearothermophilus* (Nagata, et al. Biochemistry (1998) 27, 9056) is subjected to mutagenesis by error-prone PCR according to the method of May et al. The error-prone PCR is performed in a 100 μL reaction mixture containing 0.25 ng of plasmid DNA as template dissolved in PCR buffer also containing 0.2 mM of each dNTP, 50 pmol of each primer and 2.5 units of Taq polymerase. Conditions for carrying out the PCR are as follows: 2 minutes at 94 °C; 30 cycles of 30 sec 94 °C, 30 sec 55 °C; 2 minutes at 72 °C. The PCR product is double digested with Nco I and Bgl II and subcloned into pBAD/HisA vector which has been digested with the same restriction enzymes. The resulting leucine dehydrogenase mutant library is transformed into an *E. coli* host strain LMG194 and plated on LB agar supplied with 100 μg/mL ampicillin. Individual transformants are inoculated into master plates containing 0.2 mL LB Broth with 100 μg/mL ampicillin, and growth is allowed to take place for 8 to 16 hours at 37 °C with shaking at 200 rpm. Each well in each master plate is then re-inoculated by a replica plating technique into a new second stage 96-well plate pre-loaded with the same growth media plus 2 g/L of arabinose, and growth is allowed to continue for 5-10 hours at 37 °C with shaking at 200 rpm. The second stage plates are then centrifuged at 14,000 rpm for 20 minutes, and the supernatant is decanted. The cell pellet in each well is washed with 200 µL of water. The washed cell pellet is suspended in 30 µL of B-Per After mixing, the suspension of cells in B-Per reagent is allowed to stand for 10 minutes at room temperature, and a solution having the following composition is then added to each well in the plate:

7.5 µL of a pH 6.5 solution containing 8 µg/mL of NADH 7.5 µL of a pH 6.5 50% DMSO solution containing 0.25 M 3,3-dimethyl-2-ketobutyrate 155 µL of 1 mM potassium phosphate buffer, pH 6.5, containing 100 mM ammonium chloride 1.5 µL of a 4 µg/mL solution of cresol red indicator Wells in which the color changes from an initial yellow to an orange or red color contain leucine dehydrogenase that catalyzes the reductive amination of the target 2-ketoacid 3,3-dimethyl-2-ketobutyrate. These wells are correlated to the original wells in the master plates to obtain the original clones of mutant leucine dehydrogenase that catalyzes the desired reductive amination reaction.

Example 15

Detection of an enzyme that reductively aminates the target compound 4-(methylphosphinyl)-2-ketobutyrate The procedure of Example 14 is repeated, replacing 3,3-dimethyl-2-ketobutyrate with 4-(methylphosphinyl)-2-ketobutyrate, thereby identifying at least one mutant dehydrogenase that catalyzes the desired reductive amination reaction.

Example 16

Detection of an enzyme that reductively aminates the target compound 3-(2-naphthyl)pyruvate The procedure of Example 14 is repeated, replacing 3,3-dimethyl-2-ketobutyrate with 3-(2-naphthyl)pyruvate, thereby identifying at least one mutant dehydrogenase that catalyzes the desired reductive amination reaction.

Example 17

Detection of an enzyme that reductively aminates the target compounds 3-(1-naphthyl)pyruvate The procedure of Example 14 is repeated, replacing the 3,3-dimethyl-2-ketobutyrate with 3-(1-naphthyl)pyruvate, thereby identifying at least one mutant dehydrogenase that catalyzes the desired reductive amination reaction.

Example 18

Detection of an enzyme that reductively aminates the target compound 4-phenyl-2-ketobutyrate The procedure of Example 14 is repeated, replacing 3,3-dimethyl-2-ketobutyrate with 4-phenyl-2-ketobutyrate, thereby identifying at least one mutant dehydrogenase that catalyzes the desired reductive amination reaction.

Example 19

Detection of an enzyme that reductively aminates the target compound 4,4-dimethyl-2-ketopentanoate The procedure of Example 14 is repeated replacing the 3,3-dimethyl-2-ketobutyrate with 4,4-dimethyl-2-ketopentanoate, thereby identifying at least one mutant dehydrogenase that catalyzes the desired reduction reaction.

Example 20

Detection of an enzyme that oxidizes the target compound L-tert-leucine

A gene encoding the leucine dehydrogenase from *B. stearothermophilus* is subjected to mutagenesis by error-prone PCR according to the method of May et al. The error-prone PCR is performed in a 100 µL reaction mixture containing 0.25 ng of plasmid DNA as template dissolved in PCR buffer (10 mM TRIS, 1.5 mM MgCl2, 50 mM KCl, pH 8.3), and also containing 0.2 mM of each dNTP, 50 pmol of each primer and 2.5 units of Taq polymerase. Conditions for carrying out the PCR are as follows: 2 minutes at 94 °C; 30 cycles of 30 sec 94 °C, 30 sec 55 °C; 2 minutes at 72 °C. The PCR product is double digested with Nco I and Bgl II and subcloned into pBAD/HisA vector which has been digested with the same restriction enzymes. The resulting leucine dehydrogenase mutant library is transformed into an *E. coli* host strain LMG194 and plated on LB agar supplied with 100 µg/mL ampicillin. Individual transformants are inoculated into 96-well master plates containing 0.2 mL LB Broth with 100 µg/mL ampicillin, and growth is allowed to take place for 8-16 hours at 37 °C with shaking at 200 rpm. Each well in each master plate is then re-inoculated by a replica plating technique into a new second stage 96-well plate pre-loaded with the same growth media plus 2 g/L of arabinose, and growth is allowed to continue for 5-10 hours at 37 °C with shaking at 200 rpm. The second stage plates are then centrifuged at 14,000 rpm for 20 minutes, and the supernatant is decanted. The cell pellet in each well is washed with 200 µL of water. The washed cell pellet is suspended in 30 µL of B-Per. After mixing, the suspension of cells in B-Per reagent is allowed to stand for 10 minutes at room temperature, and a solution having the following composition is then added to each well in the plate:

7.5 µL of a pH 8.0 solution containing 20 µg/ml of NAD+

7.5 µL of a pH 8.0 50% DMSO solution containing 0.25 M L-tert-leucine (S-3,3-dimethyl-2-aminobutyrate)

155 µL of 2 mM potassium phosphate buffer, pH 8.0, containing 100 mM ammonium chloride 1.5 µL of a 4 µg/ml solution of bromothymol blue indicator Wells in which the color changes from an initial blue to a yellow color contain mutant leucine dehydrogenases that catalyze the oxidation of the target amino acid. These wells are correlated to the original wells in the master plates to obtain the original clones of mutant leucine dehydrogenases catalyzing the desired oxidation reaction.

Example 21

Detection of an enzyme that oxidizes the target compound S-phosphinothricin

The procedure of Example 20 is repeated replacing the L-tert-leucine with S-phosphinothricin, thereby identifying at least one mutant alcohol dehydrogenase that catalyzes the desired oxidation reaction.

Example 22

Detection of an enzyme that oxidizes the target compound S-(2-naphthyl) alanine The procedure of Example 20 is repeated, replacing the L-tert-leucine with S-(2-naphthyl)alanine, thereby identifying at least one mutant alcohol dehydrogenase that catalyzes the desired oxidation reaction.

Example 23

Detection of an enzyme that oxidizes the target compound D-tert-leucine

The procedure of Example 20 is repeated, replacing the L-tert-leucine with D-tert-leucine, thereby identifying at least one mutant alcohol dehydrogenase that catalyzes the desired oxidation reaction.

Example 24

Detection of an enzyme that oxidizes the target compound S-4-phenyl-2-aminobutyrate The procedure of Example 20 is repeated, replacing L-tert-leucine with S-4-phenyl-2-aminobutyrate, thereby identifying at least one mutant alcohol dehydrogenase that catalyzes the desired oxidation reaction.

Example 25

Detection of an enzyme that oxidizes the target compound D-tyrosine

The procedure of Example 20 is repeated, replacing the L-tert-leucine with D-tyrosine, thereby identifying at lest one mutant alcohol dehydrogenase that catalyzes the desired oxidation reaction.

Example 26

General Procedure for Detection of an Enzyme Mutant that Reductively Aminates the Target Compound Acetophenone A gene encoding leucine dehydrogenase from *B. stearothermophilus* is subjected to mutagenesis by error-prone PCR according to the method of May, et al. The error-prone PCR is performed in a 100 $\mu$L reaction mixture containing 0.25 ng of plasmid DNA as template dissolved in PCR buffer containing 0.2 mM of each dNTP, 50 pmol of each primer and 2.5 units of Taq polymerase. Conditions for carrying out the PCR are as follows: 2 minutes at 94 $°$C; 30 cycles of 30 sec 94 $°$C, 30 sec 55 $°$C; 2 minutes at 72 $°$C. The PCR product is double digested with Nco I and Bgl II and subcloned into pBAD/HisA vector which has been digested with the same restriction enzymes. The resulting leucine dehydrogenase mutant library is transformed into an *E. coli* host strain LMG194 and plated on LB agar supplied with 100 $\mu$g/mL ampicillin. Individual transformants are inoculated into master plates containing 0.2 mL LB Broth with 100 $\mu$g/mL ampicillin, and growth is allowed to take place for 8-16 hours at 37 $°$C with shaking at 200 rpm. Each well in each master plate is then re-inoculated by a replica plating technique into a new second stage 96-well plate pre-loaded with the same growth media plus 2 g/L of arabinose, and growth is allowed to continue for 5-10 hours at 37 $°$C with shaking at 200 rpm. The second stage plates are then centrifuged at 14,000 rpm for 20 minutes, and the supernatant is decanted. The cell pellet in each well is washed with 200 $\mu$L of water. The washed cell pellet is suspended in 30 $\mu$L of B-Per. After mixing, the suspension of cells in B-Per reagent is allowed to stand for 10 minutes at room temperature, and a solution having the following composition is then added to each well in the plate:

7.5 $\mu$L of a pH 6.5 solution containing 8 $\mu$g/mL of NADH
7.5 $\mu$L of a pH 6.5 50% DMSO solution containing 0.25 M acetophenone
155 $\mu$L of 1 mM potassium phosphate buffer, pH 6.5, containing 100 mM ammonium chloride
1.5 $\mu$L of a 4 $\mu$g/mL solution of cresol red indicator Wells in which the color change from an initial yellow to an orange or red color contain leucine dehydrogenases that catalyzes the reductive amination of the target ketone acetophenone. These wells are correlated to the original wells in the master plates to obtain the original clones of mutant leucine dehydrogenase that catalyzes the desired reductive amination reaction.

Example 27

Detection of an enzyme that oxidizes the target compound S-1-phenylethylamine A gene encoding the leucine dehydrogenase from *B. stearothermophilus* is subjected to mutagenesis by error-prone PCR according to the method of May, et al. The error-prone PCR is performed in a 100 $\mu$L reaction mixture containing 0.25 ng of plasmid DNA as template dissolved in PCR buffer containing 0.2 mM of each dNTP, 50 pmol of each primer and 2.5 units of Taq polymerase. Conditions for carrying out the PCR are as follows: 2 minutes at 94 $°$C; 30 cycles of 30 sec 94 $°$C, 30 sec 55 $°$C; 2 minutes at 72 $°$C. The PCR product is double digested with Nco I and Bgl II and subcloned into pBAD/HisA vector which has been digested with the same restriction enzymes. The resulting leucine dehydrogenase mutant library is transformed into an *E. coli* host strain LMG194 and plated on LB agar supplied with 100 $\mu$g/mL ampicillin. Individual transformants are inoculated into master plates containing 0.2 mL LB Broth with 100 $\mu$g/mL ampicillin, and growth is allowed to take place for 8-16 hours at 37 $°$C with shaking at 200 rpm. Each well in each master plate is then re-inoculated by a replica plating technique into a new second stage plate pre-loaded with the same growth media plus 2 g/L of arabinose, and growth is allowed to continue for 5 to 10 hours at 37 $°$C with shaking at 200 rpm. The second stage plates are then centrifuged at 14,000 rpm for 20 minutes, and the supernatant is decanted. The cell pellet in each well is washed with 200 $\mu$L of water. The washed cell pellet is suspended in 30 $\mu$L of B-Per Bacterial Protein Extraction Reagent. After mixing, the suspension of cells in B-Per reagent is allowed to stand for 10 minutes at room temperature, and a solution having the following composition is then added to each well in the plate:

7.5 μL of a pH 8.0 solution containing 20 μg/mL of NAD+
7.5 μL of a pH 8.0 50% DMSO solution containing 0.25 M S-1-phenylethylamine
155 μL of 2 mM potassium phosphate buffer, pH 8.0, containing 100 mM ammonium chloride
1.5 μL of a 4 μg/mL solution of bromothymol blue indicator Wells in which the color changes from blue initially to yellow contain mutant leucine dehydrogenase that catalyze the oxidation of the target amine. These wells are correlated to the original wells in the master plates to obtain the original clones of mutant leucine dehydrogenases catalyzing the desired oxidation reaction.

Example 28

Detection of an enzyme that oxidizes the target compound R-1-phenylethylamine

A gene encoding the leucine dehydrogenase from *B. stearothermophilus* is subjected to mutagenesis by error-prone PCR according to the method of May, et al. The error-prone PCR is performed in a 100 μL reaction mixture containing 0.25 ng of plasmid DNA as template dissolved in PCR buffer containing 0.2 mM of each dNTP, 50 pmol of each primer and 2.5 units of Taq polymerase. Conditions for carrying out the PCR are as follows: 2 minutes at 94 °C; 30 cycles of 30 sec 94 °C, 30 sec 55 °C; 2 minutes at 72 °C. The PCR product is double digested with Nco I and Bgl II and subcloned into pBAD/HisA vector which has been digested with the same restriction enzymes. The resulting leucine dehydrogenase mutant library is transformed into an *E. coli* host strain LMG194 and plated on LB agar supplied with 100 μg/mL ampicillin. Individual transformants are inoculated into master plates containing 0.2 mL LB Broth with 100 μg/mL ampicillin, and growth is allowed to take place for 8-16 hours at 37 °C with shaking at 200 rpm. Each well in each master plate is then re-inoculated by a replica plating technique into a new second stage plate pre-loaded with the same growth media plus 2 g/L of arabinose, and growth is allowed to continue for 5-10 hours at 37 °C with shaking at 200 rpm. The second stage plates are then centrifuged at 14,000 rpm for 20 minutes, and the supernatant is decanted. The cell pellet in each well is washed with 200 μL of water. The washed cell pellet is suspended in 30 μL of B-Per. After mixing, the suspension of cells in B-Per reagent is allowed to stand for 10 minutes at room temperature, and a solution having the following composition is then added to each well in the plate:

7.5 μL of a pH 8.0 solution containing 20 μg/mL of NAD+
7.5 μL of a pH 8.0 50% DMSO solution containing 0.25 M R-1-phenylethylamine
155 μL of 2 mM potassium phosphate buffer, pH 8.0, containing 100 mM ammonium chloride
1.5 μL of a 4 μg/mL solution of bromothymol blue indicator Wells in which the color changes from blue initially to yellow contain mutant leucine dehydrogenase that catalyze the oxidation of the target amine. These wells are correlated to the original wells in the master plates to obtain the original clones of mutant leucine dehydrogenases catalyzing the desired oxidation reaction.

Example 29

Production of 1-phenylethylamine by the reductive amination of acetophenone

One hundred units of an amine dehydrogenase generated by mutagenesis and screening of leucine dehydrogenase as described in any one of Examples 26 to 28 above is incubated at 45° C. in 100 milliliters of a solution maintained at pH 6.5 containing potassium phosphate (1 millimole), NADH (0.01 millimole), ammonium formate (25 millimoles), and formate dehydrogenase from *Candida boidinii* (100 units). Acetophenone (10 millimoles) is added slowly over one hour with stirring, and the reaction is allowed to proceed for an additional 4 hours. After basification of the reaction mixture to pH 12 and extraction with methyl t-butyl ether, analysis of the reaction products is carried out by gas chromatography to determine the yield of 1-phenylethylamine. Chiral analysis is carried out by chiral gas chromatography using a ChiraDex CB column (Advanced Separation Technology, Whippany, N.J. USA).

Example 30

Production of R-1-phenylethylamine by the reductive amination of acetophenone

The method of Example 29 is carried out except that the amine dehydrogenase is an R-1-phenylethylamine dehydrogenase and the product is R-1-phenylethylamine.

Example 31

Production of S-1-phenylethylamine by the reductive amination of acetophenone

The method of Example 29 is carried out except that the amine dehydrogenase is an S-1-phenylethylamine dehydrogenase and the product is S-1-phenylethylamine.

Example 32

Production of R-1-(p-chlorophenyl)ethylamine by the reductive amination of p-chloroacetophenone The method of Example 30 is carried out except that acetophenone is replaced by p-chloroacetophenone and the product is R-1-(p-chlorophenyl)ethylamine.

Example 33

Production of S-1-(p-chlorophenyl)ethylamine by the reductive amination of p-chloroacetophenone The method of Example 31 is carried out except that acetophenone is replaced by p-chloroacetophenone and the product is S-1-(p-chlorophenyl)ethylamine.

Example 34

Production of R-1-(m-bromophenyl)ethylamine by the reductive amination of m-bromoacetophenone The method of Example 30 is carried out except that acetophenone is replaced by m-bromoacetophenone and the product is R-1-(m-bromophenyl)ethylamine.

Example 35

Production of S-1-(m-bromophenyl)ethylamine by the reductive amination of m-bromoacetophenone

The method of Example 31 is carried out except that acetophenone is replaced by m-bromoacetophenone and the product is S-1-(m-bromophenyl)ethylamine.

Example 36

Production of 1-phenylethanol by the reduction of acetophenone

One hundred units of an alcohol dehydrogenase, generated by mutagenesis and screening of the alr1 gene as described in Example 13 above, is incubated at 45EC in 100 milliliters of a solution maintained at pH 6.5 containing potassium phosphate (1 millimole), NADPH (0.01 millimole), sodium formate (25 millimoles), and a NADP-utilizing formate dehydrogenase P3 (obtained from Juelich Fine Chemcials, Juelich, Germany; catalog number 25.10; 100 units). Acetophenone (10 millimoles) is added slowly over one hour with stirring, and the reaction is allowed to proceed for an additional 4 hours. The reaction mixture is extracted with methyl t-butyl ether, and analysis of the reaction products is carried out by gas chromatography to determine the yield of 1-phenylethanol. Chiral analysis is carried out by chiral gas chromatography using a ChiraDex CB column (Advanced Separation Technology, Whippany, N.J. USA).

Example 37

Production of R-1-phenylethanol by the reduction of acetophenone

The method of Example 36 is carried out except that the alcohol dehydrogenase is determined to be an R-1-phenylethanol dehydrogenase and the product is R-1-phenylethanol.

Example 38

Production of S-1-phenylethanol by the reduction of acetophenone

The method of Example 36 is carried out except that the alcohol dehydrogenase is determined to be an S-1-phenylethanol dehydrogenase and the product is S-1-phenylethanol,

Example 39

Production of R-1-(p-chlorophenyl)ethanol by the reduction of p-chloroacetophenone

The method of Example 36 is carried out except that acetophenone is replaced by p-chloroacetophenone, the alcohol dehydrogenase is determined to be an R-1-(p-chlorophenyl)ethanol dehydrogenase and the product is R-1-(p-chlorophenyl)ethanol.

Example 40

Production of S-1-(p-chlorophenyl)ethanol by the reduction of p-chloroacetophenone

The method of Example 36 is carried out except that acetophenone is replaced by p-chloroacetophenone, the alcohol dehydrogenase is determined to be an S-1-(p-chlorophenyl)ethanol dehydrogenase and the product is S-1-(p-chlorophenyl)ethanol.

Example 41

Production of R-1-(m-bromophenyl)ethanol by the reduction of m-bromoacetophenone

The method of Example 36 is carried out except that acetophenone is replaced by m-bromoacetophenone, the alcohol dehydrogenase is determined to be an R-1-(m-bromophenyl)ethanol dehydrogenase, and the product is R-1-(m-bromophenyl)ethanol.

Example 42

Production of S-1-(m-bromophenyl)ethanol by the reduction of m-bromoacetophenone

The method of Example 36 is carried out except that acetophenone is replaced by m-bromoacetophenone, the alcohol dehydrogenase is determined to be an S-1-(m-bromophenyl)ethanol dehydrogenase, and the product is S-1-(m-bromophenyl)ethanol.

The preceding description has been presented with reference to presently preferred embodiments of the invention. Workers skilled in the art and technology to which this invention pertains will appreciate that alterations and changes in the described methods and kits may be practiced without meaningfully departing from the spirit and scope of this invention. Accordingly, the foregoing description should not be read as pertaining only to the precise methods and kits described, but rather should be read consistent with and as support to the following claims, which are to have their fullest and fair scope.

What is claimed is:

1. A method of producing a chiral amine in enantiomeric excess from a target ketone, comprising:
    screening mutated amine dehydrogenases for conversion of a target ketone to a chiral amine to identify a mutated amine dehydrogenase with activity for producing an enantiomeric excess of the chiral amine; and
    contacting the identified amine dehydrogenase with the target ketone under conditions sufficient for producing an enantiomeric excess of the chiral amine, wherein the target ketone is not a 2-ketoacid.

2. The method of claim 1 in which the target ketone is contacted with the identified amine dehydrogenase in the presence of a NAD(P)H cofactor recycling system.

3. The method of claim 1, wherein the amine dehydrogenase is an amino acid dehydrogenase.

* * * * *